(12) United States Patent
Oonuma et al.

(10) Patent No.: US 6,440,369 B1
(45) Date of Patent: *Aug. 27, 2002

(54) AUTOMATIC ANALYZER AND DISPLAY METHOD FOR AUTOMATIC ANALYZER

(75) Inventors: Mitsuru Oonuma, Tokyo; Atsushi Katayama, Kokubunji; Isamu Takekoshi, Tokyo; Isao Shindo, Hitachinaka; Kahei Shiraishi, Hitachiota; Hiromichi Sato, Hitachinaka, all of (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,655
(22) PCT Filed: Sep. 3, 1996
(86) PCT No.: PCT/JP96/02490
  § 371 (c)(1),
  (2), (4) Date: Feb. 27, 1998
(87) PCT Pub. No.: WO97/09621
  PCT Pub. Date: Mar. 13, 1997

(30) Foreign Application Priority Data

Sep. 5, 1995 (JP) ............................................. 7-227723

(51) Int. Cl.$^7$ ............................................. G01N 35/10
(52) U.S. Cl. ............................ 422/64; 422/63; 436/43; 436/47
(58) Field of Search ........................ 422/63, 64; 436/43, 436/47

(56) References Cited

U.S. PATENT DOCUMENTS

| | | | | |
|---|---|---|---|---|
| 4,234,540 A | * | 11/1980 | Ginsberg et al. ............... 422/64 |
| 4,276,258 A | | 6/1981 | Ginsberg et al. | |
| 4,346,056 A | * | 8/1982 | Sakurada ...................... 422/64 |
| 4,483,823 A | * | 11/1984 | Umetsu et al. ................ 422/64 |
| 4,774,055 A | | 9/1988 | Wakatake et al. | |
| 4,919,887 A | * | 4/1990 | Wakatake ...................... 422/67 |
| 4,961,906 A | * | 10/1990 | Andersen et al. ........... 422/102 |
| 4,965,049 A | * | 10/1990 | Lillig et al. ................. 422/68.1 |
| 5,104,808 A | * | 4/1992 | Laska et al. ................... 436/48 |
| 5,147,610 A | * | 9/1992 | Watanabe et al. ............. 422/64 |
| 5,314,825 A | * | 5/1994 | Weyrauch et al. ............. 436/43 |
| 5,424,036 A | | 6/1995 | Ushikubo | |
| 5,424,212 A | * | 6/1995 | Pinsl-Ober et al. ........... 436/50 |
| 5,677,188 A | * | 10/1997 | Mitsumaki et al. ........... 436/47 |
| 5,773,662 A | * | 6/1998 | Imai et al. ..................... 436/50 |
| 5,789,252 A | * | 8/1998 | Fujita et al. .................. 436/49 |
| 5,855,847 A | * | 1/1999 | Oonuma et al. .............. 422/64 |

FOREIGN PATENT DOCUMENTS

| | | |
|---|---|---|
| CA | 2171659 | 9/1996 |
| EP | 0 041 378 A1 | 12/1981 |
| EP | 0 282 601 A1 | 9/1988 |
| WO | WO93/20444 | 10/1993 |

\* cited by examiner

Primary Examiner—Jill Warden
Assistant Examiner—Kathryn Bex
(74) Attorney, Agent, or Firm—Antonelli, Terry, Stout & Kraus, LLP

(57) ABSTRACT

A small automatic analyzer in which a specimen disc 12 and a reagent disc 22 are disposed at different positions in a depth direction in a this-side area of an upper surface of an analyzer housing 40, a reaction disc 3 is disposed backward from the specimen disc 12 between the specimen disc 12 and the reagent disc 22, a specimen extracting and injecting unit 14 is disposed between the reaction disc 3 and the specimen disc 12, a reagent extracting and injecting unit 24 is disposed between the reaction disc 3 and the reagent disc 22, the specimen and reagent extracting and injecting units 14 and 24 are arranged at different positions in an oblique direction, the reaction disc 3, specimen disc 12 and reaction disc 22 each have a separate cover therefor, and the specimen extracting and injecting unit 14 and the specimen extracting and injecting unit 24 have a common cover therefor.

6 Claims, 14 Drawing Sheets

AUTOMATIC ANALYZER AND DISPLAY METHOD FOR AUTOMATIC ANALYZER

TECHNICAL FIELD

The present invention relates to automatic analyzer and more particularly to an automatic analyzer for use with a biochemical examination or immunity examination wherein a train of reaction containers turns across an optical path of a photometer.

BACKGROUND ART

A conventional automatic analyzer, for example, disclosed in JP-B2-59-22905, is effective in that no extracting and injecting mechanism is required to be provided for each of the reagents and only two extracting and injecting mechanisms are used to thereby simplify the mechanism. Another case, JP-A-6-88828, discloses an automatic analyzer in which, in order to prevent contamination between reagents and to improve the processing ability of the analyzer so that all reactions are carried out in parallel in the same time, reaction containers are disposed in a doubly or triply concentric circle with the respective trains of reaction containers being independent of each other, wherein each of the reaction containers is washed in each reactive process to thereby achieve a continuos process. One embodiment of those analyzers is disclosed in Japanese registered design No. 782418.

In the conventional analyzers, their miniaturization has not been studied, so that they each occupy a large space. Reduction in the measurement time and diversification of measurement items has been studied, but no arrangement of a control panel which controls the analyzer and a display device has been studied. Thus, they are not satisfactory in terms of easy operation, safety and/or prevention of misoperations.

DISCLOSURE OF THE INVENTION

It is an object of the present invention to provide an automatic analyzer which is miniaturized so as to be easily carried and whose components are rationally arranged so that they are safe and easily operated.

Another object of the present invention is to provide a display method for an automatic analyzer in which an instruction can be inputted to a display unit while watching same.

One of the measures for solving the above problem is to provide an automatic analyzer comprising specimen containing means, reagent containing means, extracting and injecting means, and analysis means, wherein a specimen is reacting with a reagent in a reaction container, the reacted reaction liquid is analyzed by the analysis means, the specimen containing means and the reagent containing means are disposed in an oblique manner in a thi side area of the analyzer, the reaction container is disposed backward from the specimen containing means and the reagent containing means between the specimen containing means and the reagent containing means.

Another one of the means for solving the problem is to provide covers for covering separately the specimen holding means, reagent holding means and extracting and injecting means.

Still another one of the means for solving the problem is to dispose an input/output device for an automatic analyzer with display means for displaying information on the analyzer, on this side of the reagent holding means.

In the above-mentioned one of the means for solving the problem, the distance between any two of the specimen holding means, the reagent holding means and the reaction container are substantially minimum. As a result, the specimen extracting and injecting means and the reagent extracting and injecting means are arranged in a compact manner. In addition, by disposing the input/output device on this side of the reagent holding means, the components of the automatic analyzer are arranged in a compact manner in transverse and deep directions, so that the input/output device can be manipulated while a specimen is being set, easy operation is performed, and high safety is ensured.

BEST MODE FOR CARRYING OUT THE INVENTION

One embodiment of the automatic analyzer according to the present invention will next be described with respect to the accompanying drawings.

Figure 1:
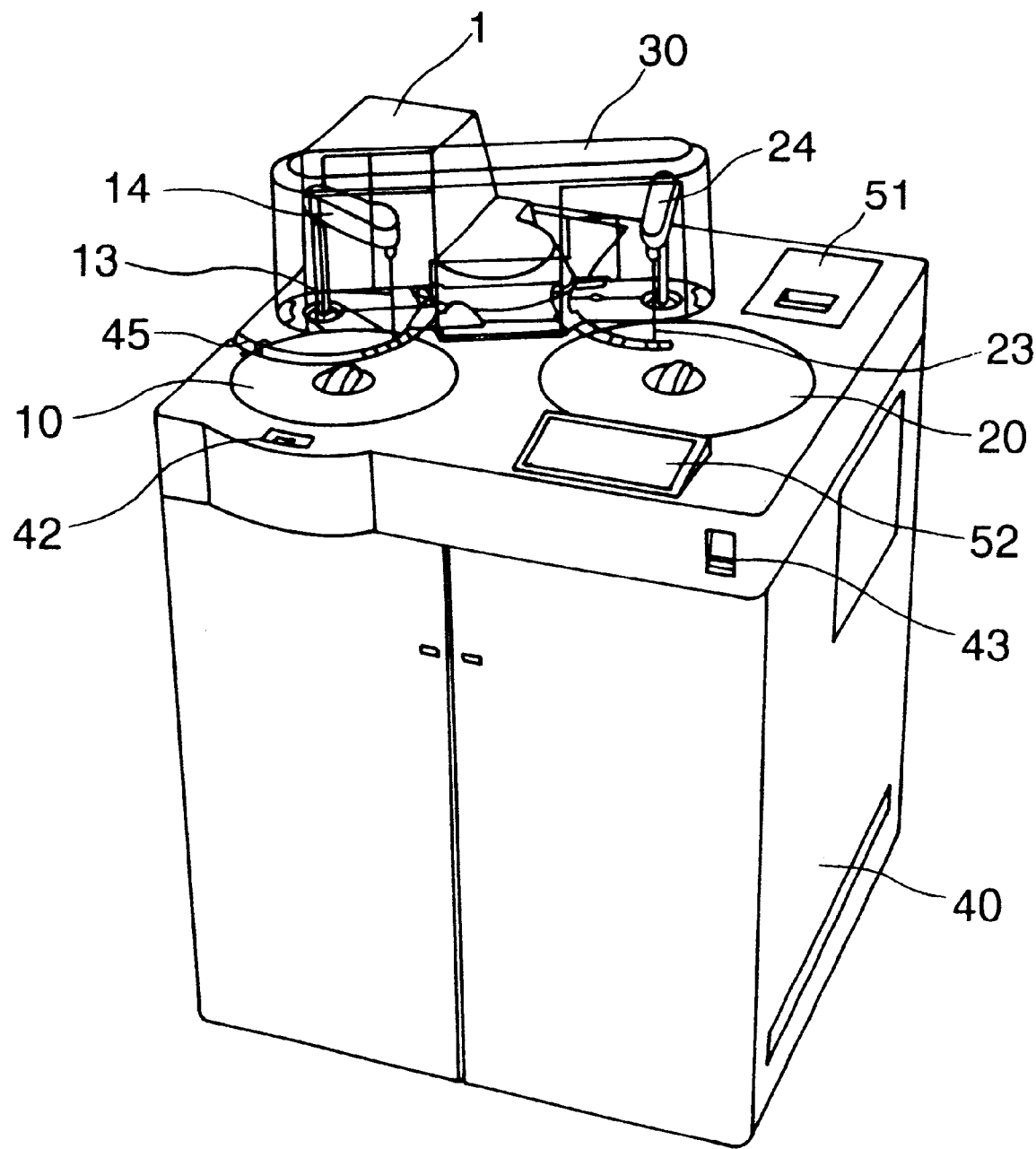
FIG. 1 is a perspective view of an automatic analyzer as one embodiment of the present invention.
Figure 2:
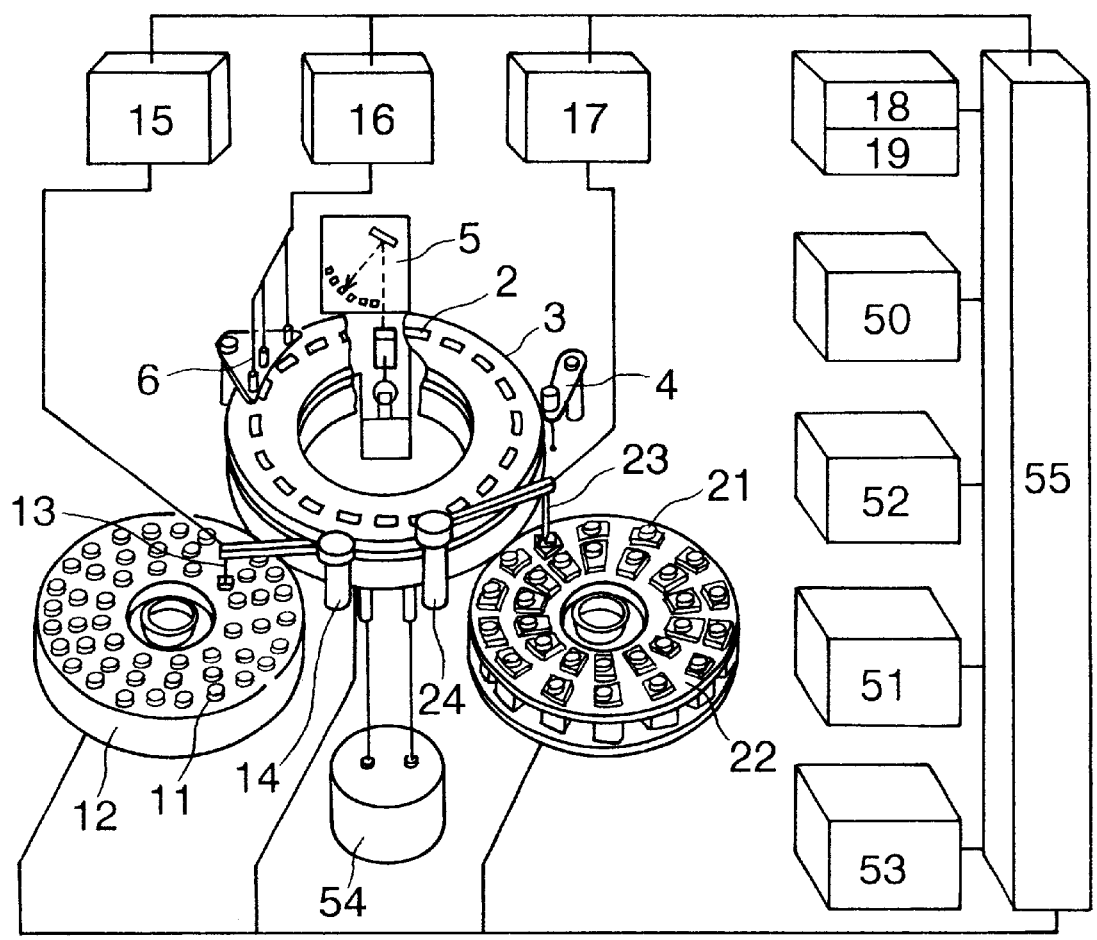
FIG. 2 illustrates the principles of the main components of the automatic analyzer.
Figure 3:
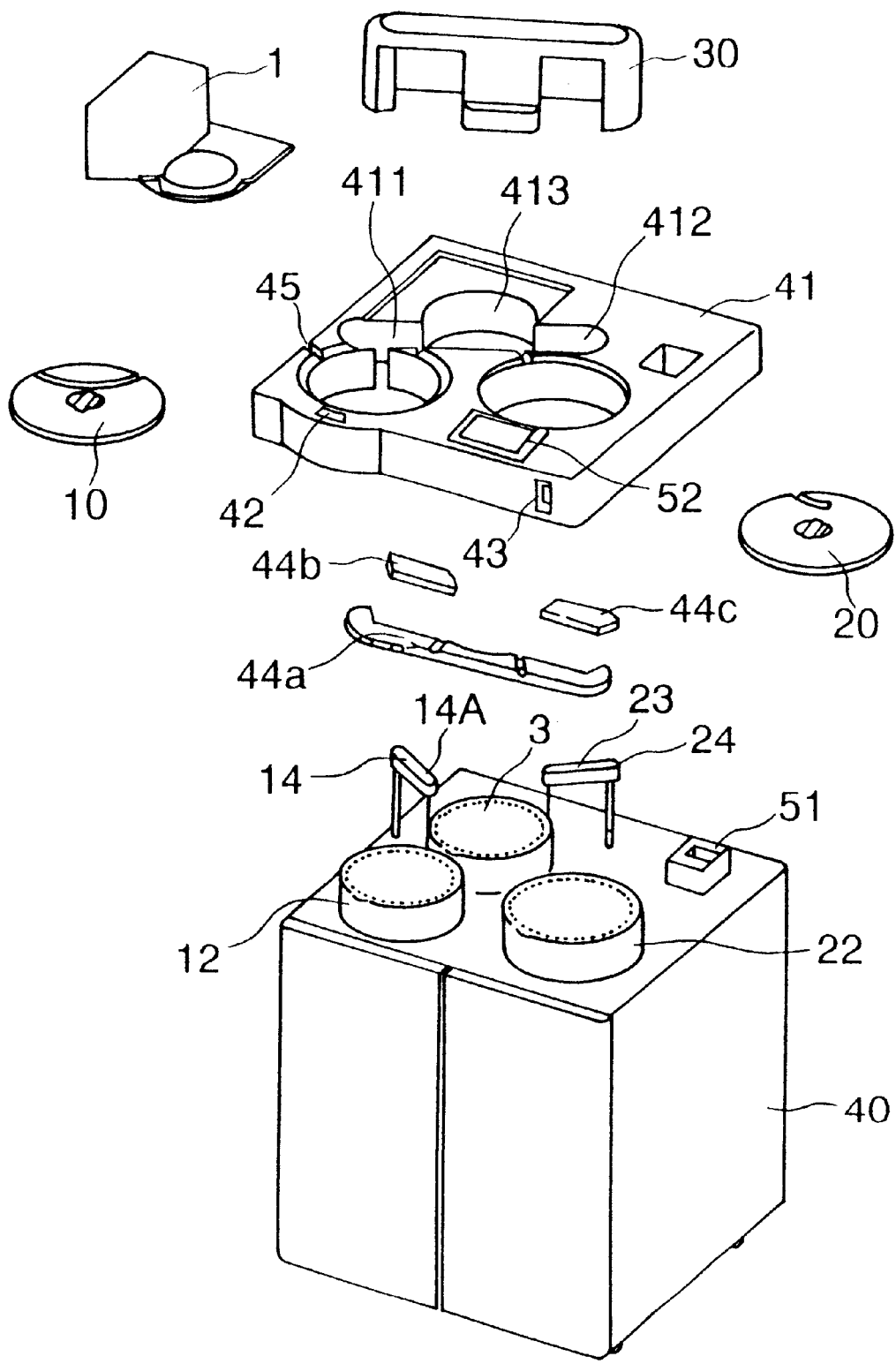
FIG. 3 is an exploded view of the automatic analyzer of FIG. 1.

FIG. 1 is a perspective view of the automatic analyzer as one embodiment of the present invention. FIG. 2 illustrates the principles of the main components of the automatic analyzer of FIG. 1. FIG. 3 is an exploded view of the automatic analyzer of FIG. 1.

First, in FIG. 2, the principles of the main components of the inventive automatic analyzer will be described. A plurality of square transparent plastic reaction containers 2 is held in a rotary reaction disc 3. A plurality of reagent containers 21 is held in a rotary reagent disc 22. A plurality of specimen containers 11 for a plurality of materials to be tested and a plurality of specimen containers for a plurality of standard materials are set in a rotary specimen disc 12.

A specimen sampling mechanism (hereinafter referred to as a specimen extracting and injecting unit) 14 and a micro syringe mechanism 15 which cooperate to draw from a specimen container 11 at a predetermined position on the specimen disc 12 a predetermined quantity of specimen liquid based on input specimen information into a nozzle 13 held by a movable specimen arm and to inject the drawn quantity of specimen liquid into a reaction container 2 at a predetermined position on the reaction disc 3. A single reagent pipetting mechanism (hereinafter referred to as a reagent extracting and injecting unit) 24 and a syringe mechanism 17 are provided. On the basis of inputted specimen information, the reagent disc 22 rotates and its stopping position is controlled. The reagent extracting and injecting unit 24 and the syringe mechanism 17 cooperate to draw a predetermined quantity of a reagent based on inputted information into a reagent nozzle 23 held on a movable arm from a regent bottle at a reagent draw position on the reagent disc 22 and to inject the drawn reagent into a reaction container 2 at the reagent inject position on the reaction table 3. The position at which the reaction liquid contained in the reaction container is stirred by a stirring mechanism 2 coincides with a position on the reaction disc 3 where the reagent is injected.

The analyzer is further provided with a hig[0088] speed multiwavelength photometer 5 which measures an optical absorption degree of each reaction container 2 which traverses an optical axis with a predetermined wavelength based on the inputted information when the reaction disc 3 is rotated, a washing nozzle mechanism 6 which washes the reaction container 2 after the measurement has ended, a wash-water feed/drain pump mechanism 16, an LG amplifier 18, an A/D converter 19, a computer 50 which controls the operations of the respective mechanisms and processes data, an output printer 51, an LCD 52 with an input/output and display touch panel, a floppy disk mechanism 53 which stores/contains a program, measurement conditions and data, a circulation-type constant-temperature water tank 54 for holding the respective reaction containers 2 on the reaction disc 3 at a predetermined temperature, and an interface 55 which connects the respective mechanisms and the computer 50.

The specified arrangement of the components of the automatic analyzer will be described next. In FIGS. 1 and three, some of the components of the analyzer described with respect to FIG. 2 are included in a housing 40 and some are exposed on an upper surface of the housing 40. The specimen disc 12 is disposed in the left end portion of an operator's-side (hereinafter referred to as "this-side") area of the upper surface of the housing 40. The reagent disc 22 is disposed on the right-hand side of the specimen disc 12 on the upper surface of the housing 40. The output printer 51 is disposed on the opposite side of the reagent disc 22 from the operator's side (hereinafter referred to as "backward side").

The reagent disc 22 has a larger diameter than the specimen disc 12. The specimen disc 12 is disposed in center on this side compared to the reagent disc 22. The reaction disc 3 is disposed backward from the specimen disc 12 and closer in center to the reagent disc 22 than he specimen disc 12. As will be described in detail later, he specimen extracting and injecting unit 14 is disposed so that the reaction disc 3 and the specimen disc 12 are set within the rotational range of the arm 14A thereof. The specimen extracting and injecting unit 14 is disposed at a position where the distance between the left-hand end of the upper surface of the housing 40 and the position where the specimen extracting and injecting unit 14 is disposed is shorter than the length of the arm 14A. The reagent extracting and injecting unit 24 is disposed backward from the reagent disc 22 with the reaction disc 3 and the reagent disc 22 being set within the rotational range of the arm 23 of the reagent extracting and injecting unit 24.

Thus, the respective discs 3, 12 and 22 are disposed close to each other. The specimen and reagent extracting and injecting units 14 and 24 disposed backward from the specimen and reagent discs 12 and 22 are each disposed at a position in an oblique direction. As a result, the width and depth of the analyzer are reduced, the whole analyzer becomes compact, and the area in which the analyzer is set is reduced.

Provided on an upper surface of the housing 40 is a ceiling plate 41 separable from the housing 40 and having an upper smooth surface. The ceiling plate 41 has at appropriate positions openings through which the reaction disc 3, specimen disc 12, reagent disc 22, specimen extracting and injecting unit 14, reagent extracting and injecting unit 24, and output printer 51 are exposed. Since the ceiling plate 41 has the upper smooth surface, the upper surface of the whole analyzer obtained when the ceiling plate 41 is attached to the housing 40 becomes smooth. Thus, the upper surface of the housing is easily cleaned as requested.

The input/output and display touch-paneled LCD 52 is disposed in the vicinity of the reagent disc 22 in the this-side area of the housing 40. A safety indicator 42 is disposed in the vicinity of the specimen disc 12 in the this-side area of the upper surface of the housing 40. A conveyance line groove 45 is provided on the left side of the specimen disc 12 on the ceiling plate 41. A secondary power supply switch 43 is disposed on a vertical this-side edge of the ceiling plate 41. A primary power supply switch (not shown) is disposed on a vertical back edge of the ceiling plate 41.

The conveyance line groove 45 is continuous to a groove 46a disposed in a specimen disc cover 10 to be also described later and is disposed so as to extend along the orbit of the rotational mechanism of the specimen extracting and injecting unit 14. When a second device such as, for example, a centrifuge, is connected to the left side of the housing 40, as viewed from this side, for using purposes, the specimen can be moved continuously from the second device to the specimen disc 12 or vice versa, via the groove.

Provided in the openings in the ceiling plate 41 are a cover 1 which covers the reaction disc 3, a cover 10 which covers the specimen disc 12, a cover 20 which covers the reagent disc 20, and a transparent cover 30 which covers the specimen and reagent extracting and injecting units 14 and 24. As described above, the disc covers 1, 10 and 20 and the extracting and injecting unit cover 30 are provided separately. Thus, when a cover for any particular element is opened, the covers for all other elements which are not required to be exposed remain closed whereas when a large cover which covers the conventional whole analyzer is opened, all its components including ones which are not to be used are exposed. Therefore, the operator is prevented from touching a specimen or the extracting and injecting unit(s), and hence safety is further improved in the use of the analyzer. Since the extracting and injecting mechanism cover 30 is transparent, the operator can eternally confirm the movement of the extracting and injecting mechanism. Thus, safety in the use of the analyzer is further improved.

In addition, since the covers 1, 10, 20 and 30 are provided separately, they are each required only to have a minimum required area. As a result, productivity of the covers increases and the upper surface of the analyzer becomes compact.

While the extracting and injecting mechanism cover 30 has been illustrated as transparent, it may be made of a material having such transparency, for example, translucence, that the inside of the extracting and injecting mechanism cover 30 is confirmed visually.

The ceiling plate 41 has an opening 411 which is composed of an elongated opening 412 in which the specimen and reagent extracting and injecting units 14 and 24 are disposed, and a circular opening 413 for the reaction disc.

An elongated member 44a is fitted into the elongated opening. Members 44b and 44c are fitted over the member 44a so that opposing ends of the members 44b and 44c each form a curve which coincides with a circular opening 413. By removing the respective disc covers 1, 10 and 20, and the extracting and injecting mechanism cover 30 and the extracting and injecting mechanism bases 44a, 44b and 44c when the analyzer malfunctions, the ceiling plate 41 can be removed from the housing 40 without removing the arms of the specimen and reagent extracting and injecting units 14 and 24 to thereby expose the respective components easily and hence complete easily arrangements to repair required components.

While in the particular embodiment the extracting and injecting mechanism base 44 has been illustrated as composed of the three members, it is possible to expose the opening in the ceiling plate 41 in which the extracting and injecting mechanism base 44 is set. The extracting and injecting mechanism base 44 may be composed of two members, or the extracting and injecting mechanism base 44 may be composed of a single member having notches on portions corresponding to the extracting and injecting units 14 and 24.

Figure 4:
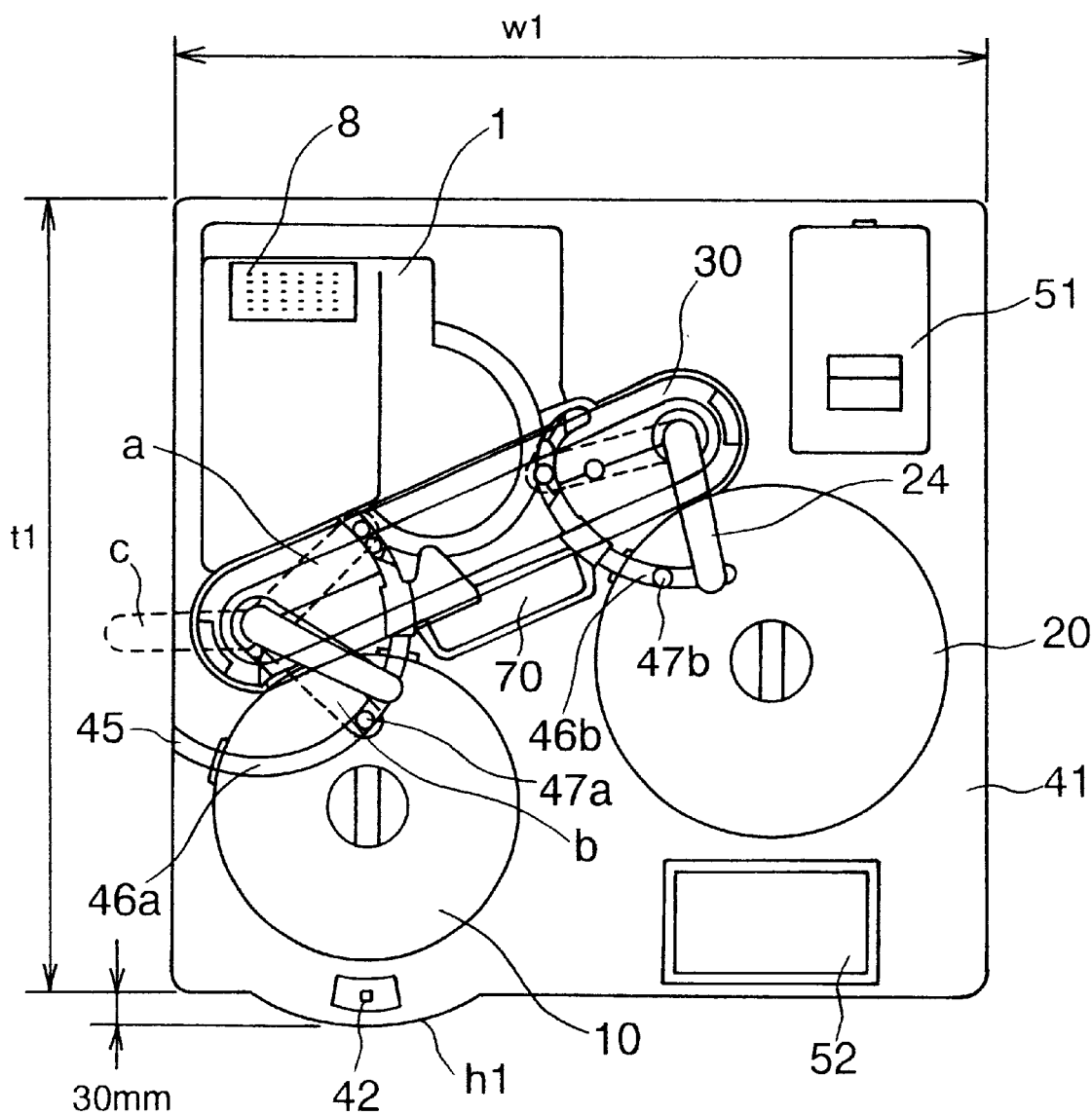
FIG. 4 is a plan view of the automatic analyzer of FIG. 1.

FIG. 4 is a plan view of the automatic analyzer of FIG. 1. In FIG. 4, the ceiling plate 41 has a parially-circular projection h1 of 30 mm concentric with the specimen disc 12 and extending this side of the specimen disc 12 and having a flat surface portion of the housing 40 on each side of the projection. Disposed in the projection h1 is a safety indicator 42 which indicates the movable state of the specimen disc 12. The safety indicator 42 is unlighted when the specimen disc 12 is at a stop or when the arm of the specimen extracting and injecting unit 14 is at a stop on the side of the reaction disc 3 whereas a green LED of the safety indicator 42 is lighted up when the specimen disc 12 or the arm of the specimen extracting and injecting unit 14 is in the movable state. Thus, when the operator approaches the analyzer to set a specimen in the specimen disc 12, the operable state of the analyzer is reported to the operator to arouse his or her attention. Since the this-way area of the specimen disc 12 projects, the operator can easily recognize the position of the specimen disc 12 to thereby prevent missetting.

While in the present embodiment the color of the LED of the safety indicator 42 has been indicated as green, the present invention is not limited to this particular case. For example, it may be red, blue or another color. The projection h1 of the ceiling plate 41 is required to have such a size that its projection can be recognized visually, and to have a flat housing surface portion on each side of the projection h1. The projection h1 is required to be in a range of 10–50 mm. In addition, the projection hi and safety indicator 42 are required to be in the vicinity of the specimen disc 12, or may be disposed, for example, laterally from the specimen disc 12.

The reaction disc cover 1 has slits 8 in an area thereof remote backward from the reaction disc cover 1 through which slits the open air enters into below the reaction disc cover 1. In the analyzer, a reaction tank 7 to be described later in more detail is maintained at a constant temperature of 37° C.—which represents the temperature of a human body. The slits 8 serve to prevent moisture from condensing into a waterdrop below the reaction disc cover 1. While in the embodiment the slits 8 are illustrated as square, they may be formed in a lattice or be slit-like.

While it has been illustrated that the whole analyzer becomes compact and occupies a reduced installation area due to the aforementioned arrangement of the components, the housing 40 of the inventive analyzer has a width w1 and a depth t1 which are each 720 mm. A single hinged door provided at a doorway to a general building or to its room from its passage has a size of about 780–900 mm. Since the dimensions of the housing 40 are 720 mm, the analyzer can be carried into an examination room without dismantling the analyzer. While in the embodiment the dimensions of the housing 41 have been illustrated as 720 mm, its width and depth w1 and t1 are not necessarily required to be the same, and should be in a range of 780–900 mm.

Figure 5:
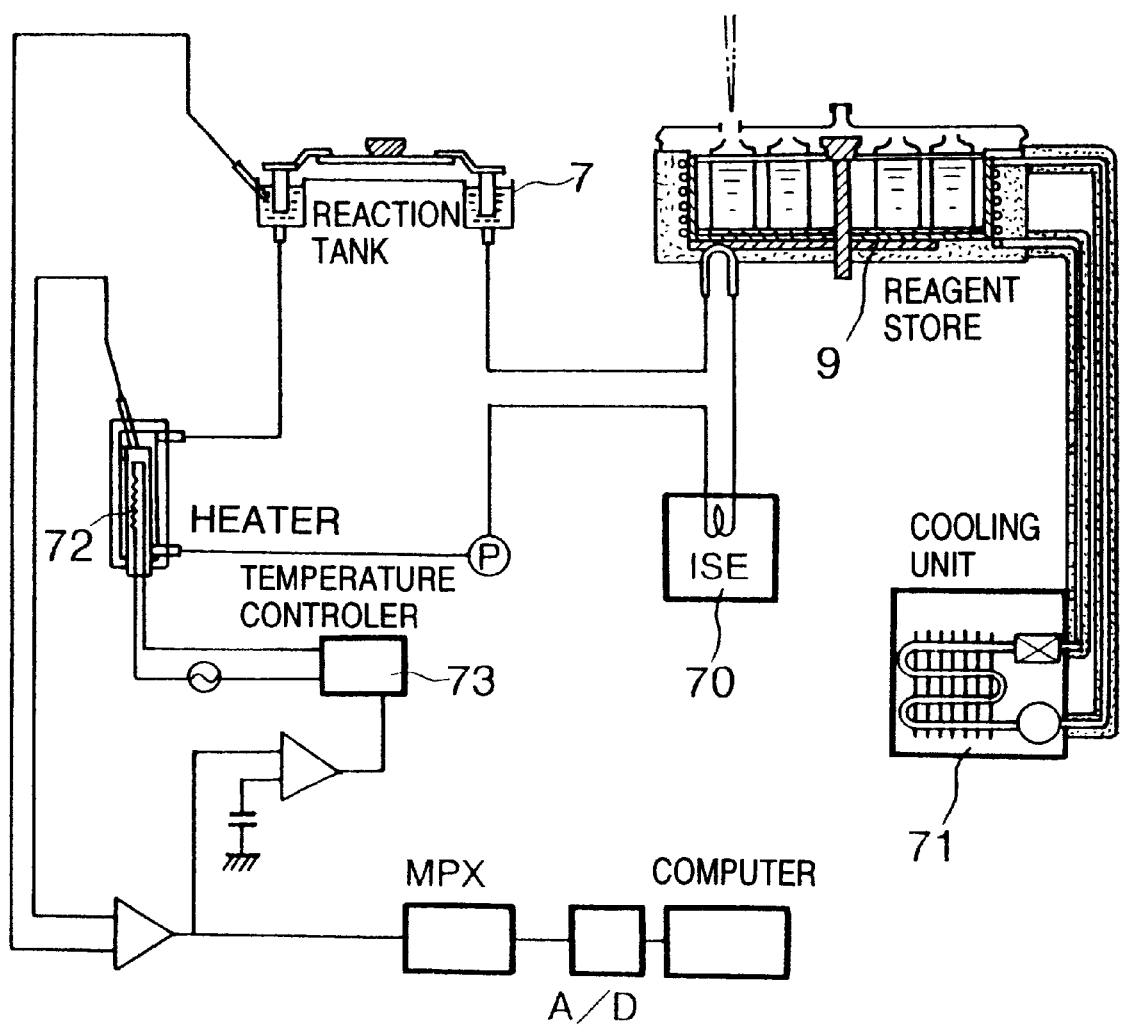
FIG. 5 illustrates a warm water route of the automatic analyzer of FIG. 1.

FIG. 5 shows a warm water route of the automatic analyzer of FIG. 1. As shown in FIG. 4, an electrolytic analyzing unit 70 is disposed among the reaction disc 3, specimen disc 12 and reagent disc 22. The electrolytic analyzing unit 70 is used to analyze a quantity of blood to measure its quantities of choline, potassium, sodium, etc., and is required usually to be kept at a constant temperature of 37° C. close to the human body' temperature. In FIG. 5, the housing 40 contains the reaction tank 7, electrolytic analyzing unit 70, reagent store 9, heater 72, temperature controller 73, and cooling unit 71. The heater 72 feeds warmed water to the reaction tank 7 and the electrolytic analyzing unit 70 to maintain the reaction tank 7 and the electrolytic analyzing unit 70 at a constant temperature. Since the reaction tank 7 is arranged close to the electrolytic analyzing unit 70, the lengths of pipes through which warm water is fed via a heater 72 to the respective tank and analyzing unit 7 and 70 are reduced. Thus, the manufacturing cost of the analyzer is reduced, its repairing is simplified, and the whole analyzer is reduced in size.

The relationship among the specimen disc cover 10, the reagent disc cover 20, and the rotational ranges of the arms of the specimen and reagent extracting and injecting units 14, and 24 will be described next.

Figure 6:
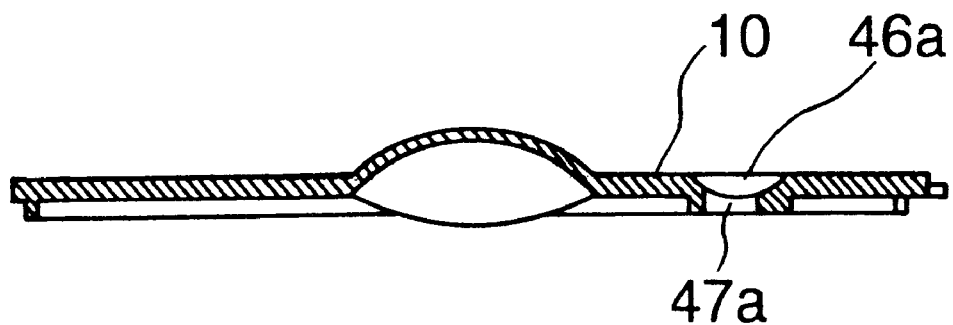
FIG. 6 is a cross-sectional view of a specimen disc cover.
Figure 7:
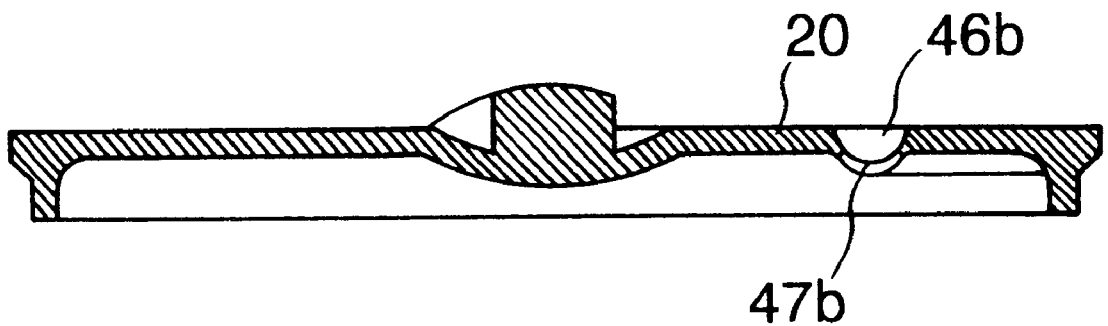
FIG. 7 is a cross-sectional view of a reagent disc cover.

FIG. 6 is a cross-sectional view of the specimen disc. FIG. 7 is a cross-sectional view of the reagent disc. In FIGS. 4, 6 and 7, the reagent disc cover 10 has an upper flat surface with a nozzle guard groove 46a extending from the reaction-disc-side end of the specimen disc cover 10 to the left end of the housing 40 as viewed from this side along the rotational orbit of the arm of the specimen. Provided in the nozzle guard groove 46a is an opening 47a at the same position as the specimen container 11 into which the nozzle 13 of the specimen extracting and injecting unit 14 is inserted.

The nozzle guard groove 46a serves to prevent the operator's finger from being held in a gap formed between the ceiling plate 41, specimen disc 12, and the nozzle 13 of the specimen extracting and injecting unit 14. When setting the specimen is completed, the specimen can be fed, with the specimen disc cover 10 being set in the specimen disc 12. Thus, dust or the like is prevented from depositing on the specimen.

The reagent disc cover 20 has a flat surface which has a nozzle guard groove 46b extending along a rotational orbit of the arm 23 of the reagent extracting and injecting unit 24 with the nozzle guard groove 46b having an opening 47b at the same position as the reagent container 21 into which opening 47b the nozzle 23 of the reagent extracting and injecting unit 24 is inserted. The nozzle guard groove 47b serves to prevent the operator's finger from being held in a gap formed between the ceiling plate 41, the reagent disc 22, and the nozzle 23 of the reagent extracting injecting unit 24. When setting the reagent is completed, the reagent can be fed, with the reagent disc cover 20 being set in the reagent disc 22. Thus, dust or the like is prevented from depositing on the reagent, the effect of holding the reagent at a low temperature (usually, in a range of 8–12° C.) is improved, and the reagent is prevented from evaporation.

The specimen disc cover 10 and the reagent disc cover 20 are fitted to the discs 12 and 22, respectively, in different manners. The nozzle guard grooves 46a and 46b coincide in shape with corresponding grooves in the reaction disc 3, so that the grooves 46a and 46b are prevented from being combined with noncorresponding grooves.

The specimen extracting and injecting unit 14 is attached at such a position that the distance between that position and the left edge of the upper surface of the housing 40 as viewed from this side is shorter than the length of the arm 14A of the specimen extracting and injecting unit 14 and hence that the arm position a on the side of the reaction disc 3, the arm position b on the side of the specimen disc 12, and the arm position con the left side of the housing 40 are within the rotational orbit of the arm 14A. Thus, when a second device is set and used on the left side of the analyzer as viewed from this side of same with the specimen disc cover 10 being set, the nozzle 13 of the specimen extracting and injecting unit 14 passes continuously through the nozzle guard groove 46a and the conveyance line groove 45. By adjusting the rotational range of the arm of the specimen extracting and injecting unit 14, the specimen, etc., can be conveyed continuously from the second device to the specimen disc 12 and the reaction disc 3.

Figure 8:
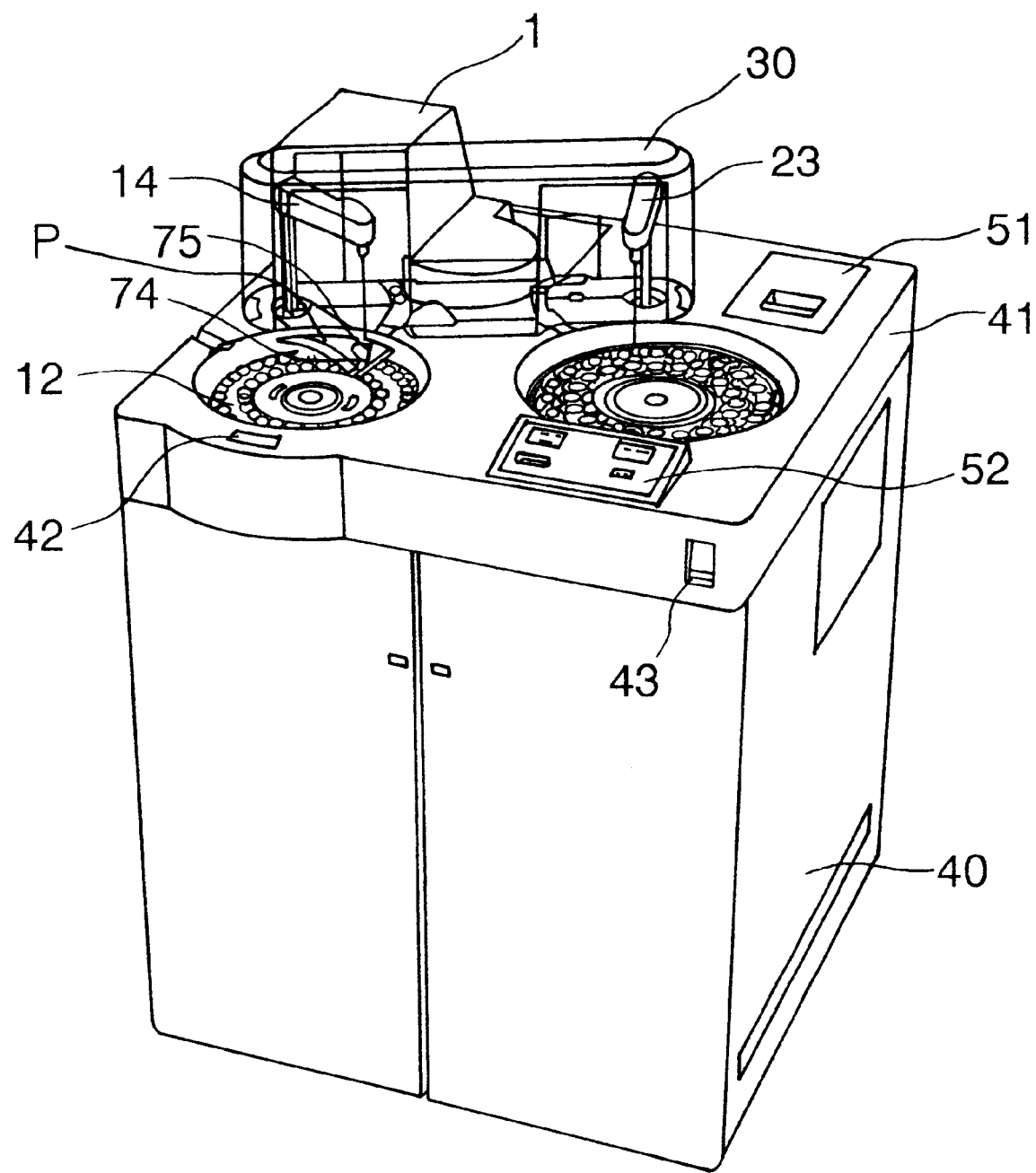
FIG. 8 is a perspective view of the automatic analyzer of FIG. 1 with covers for a specimen and a reagent disc being removed.

FIG. 8 is a perspective view of the analyzer of FIG. 1 with the specimen and reagent disc covers being removed. In FIG. 8, a shutter 74 is provided on the side of the reaction disc 3 in an opening in the ceiling plate 41 which encloses the specimen 12. The shutter 74 is triable around a pivot P. When the specimen disc cover 10 is removed, the shutter 74 extends from the inside of the ceiling plate 41 toward the specimen disc 12 whereas when the cover 10 is attached to the specimen disc 12, the shutter 74 is received below the ceiling plate 41. The shutter 74 has an opening 75 at the same position as the specimen container 11 into which opening the nozzle 13 of the specimen extracting and injecting unit 14 is inserted.

As described above, the shutter 74 automatically extends and is received below the ceiling place 41 when the specimen disc cover 10 is attached and removed, respectively, prevents the operator from touching the nozzle 13 of the specimen extracting and injecting unit 14 when the operator sets a specimen container 11 in the specimen disc 12, and closes a place in which the specimen container 11 should not be set to thereby prevent the specimen from being wrongly set.

While in the present embodiment the shutter 74 extends and is received below the ceiling plate 41 due to removal and attachment of the specimen disc cover 10, the operation of the shutter may be performed in conjunction with the operation of the specimen extracting and injecting unit 14 or the operation of the power supply of the analyzer, or a switch for commanding the operation of the shutter 74 may be provided newly.

Figure 9:
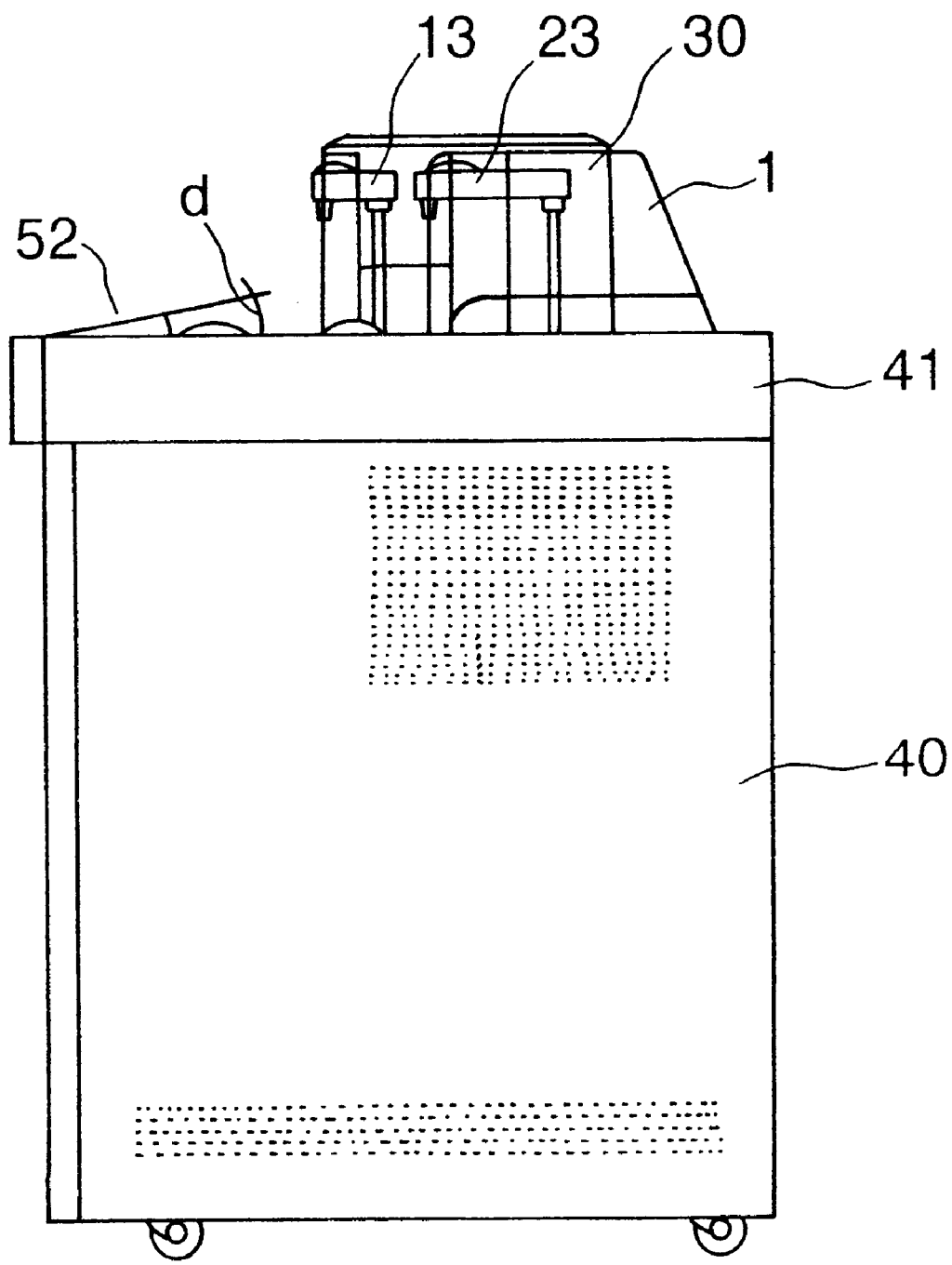
FIG. 9 is a side view of the automatic analyzer of FIG. 1.

FIG. 9 is a side view of the automatic analyzer of FIG. 1. In FIG. 1, the touch-paneled LCD 52 for inputting/outputting and displaying purposes has an oblique surface d extending backward from this side at an angle of 10 degrees. In the oblique surface d, the display is composed of liquid crystals and prevents external light from entering the display screen at right angles, so that the liquid crystal display screen is easy to watch. The touch panel is also easy to push with a finger for manipulating purposes.

While in the embodiment the oblique surface d is illustrated as at 10 degrees, it may be set at any angle in a range of 3–15 degrees.

Figure 10:
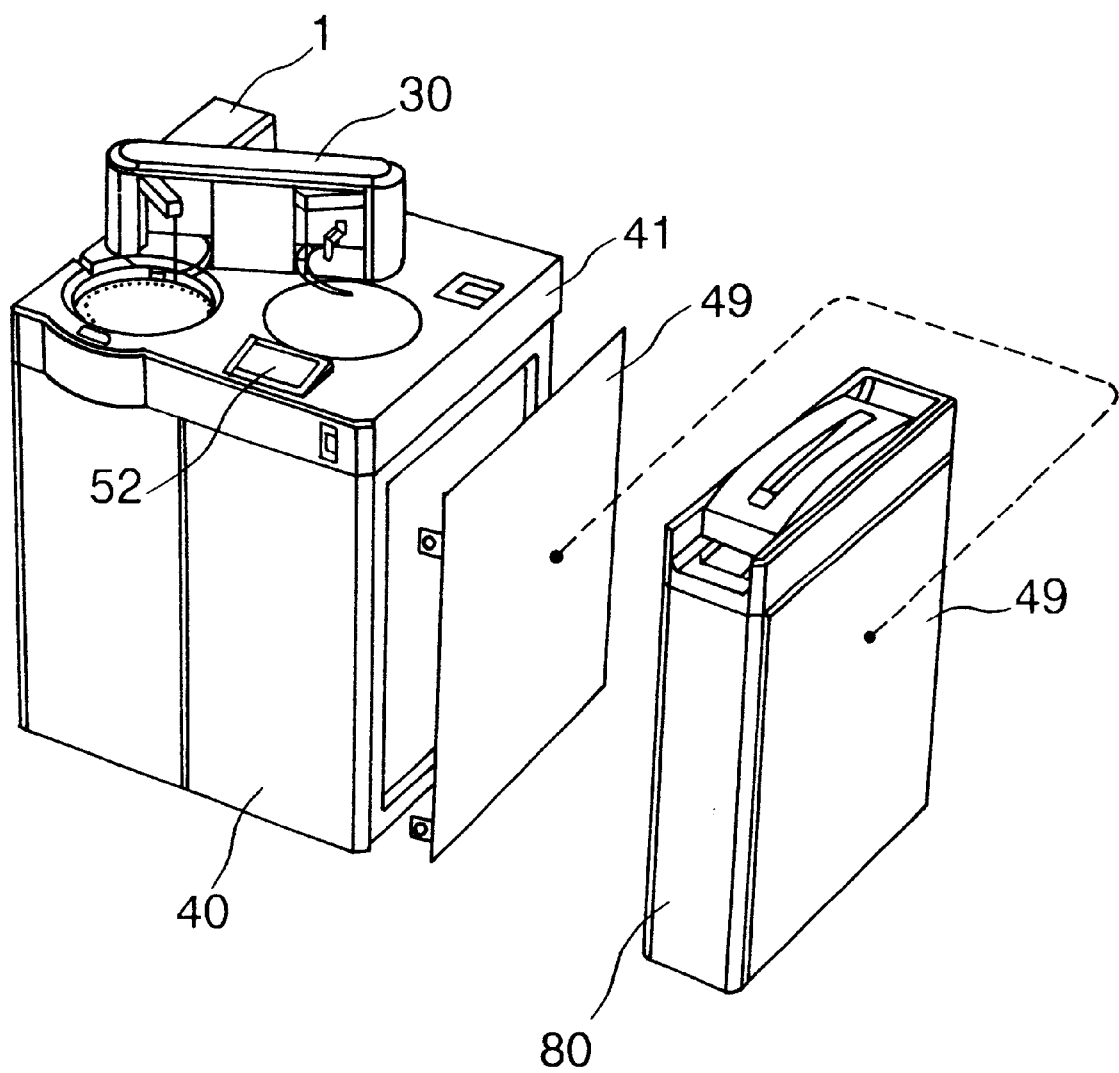
FIG. 10 is a perspective view of the automatic analyzer of FIG. 1 with an emergent examination device additionally provided.

FIG. 10 is a perspective view of the automatic analyzer of FIG. 1 and an emergent examination device 80 provided side by side with the analyzer. Although a specified operating process will be described later, each of the liquid specimens which are beforehand entered is analyzed on the basis of analysis items or item select information. When a liquid specimen is analyzed on the basis of item select information which is not entered beforehand (hereinafter referred to as "emergent examination"), the emergent examination device 80 is connected to the housing 40 of the analyzer for using purposes. The emergent examination device 80 is the same in height and depth as the housing 40, and usually has no side covers so that a side cover 49 is removed from the housing 40 of the analyzer for exposing purposes, the emergent examination device 80 is attached to the exposed side of the housing 40, and the removed side cover 49 is attached to the opposite side of the emergent examination device 80 from the housing 40 for using purposes. Thus, the emergent examination device 80 is not required to have a side cover and hence the production cost is reduced.

A typical use of the automatic analyzer as the embodiment of the present invention will be described next.

Figure 11:
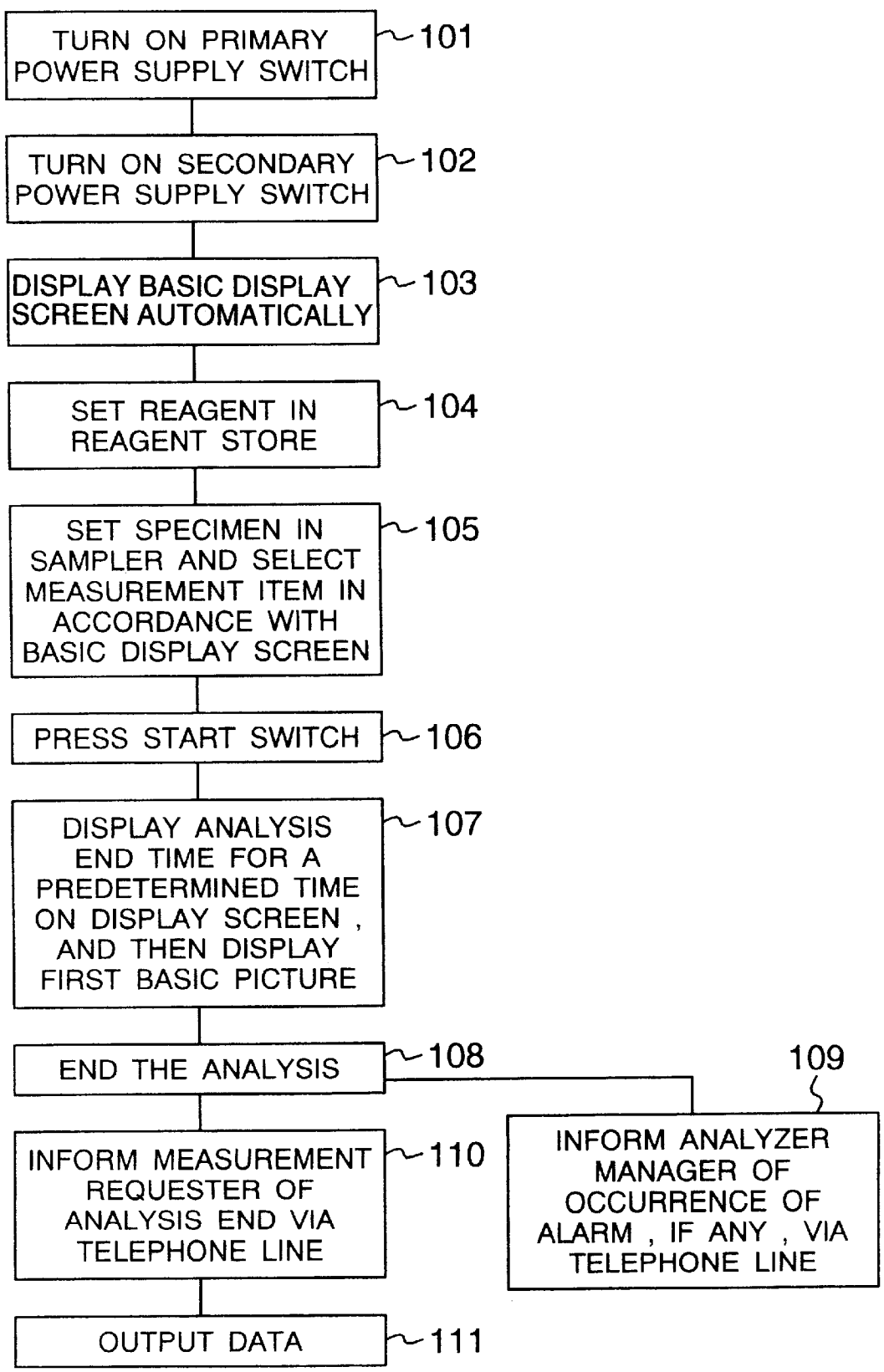
FIG. 11 is a flow chart of an analyzing process and operation of the present analyzer.
Figure 12:
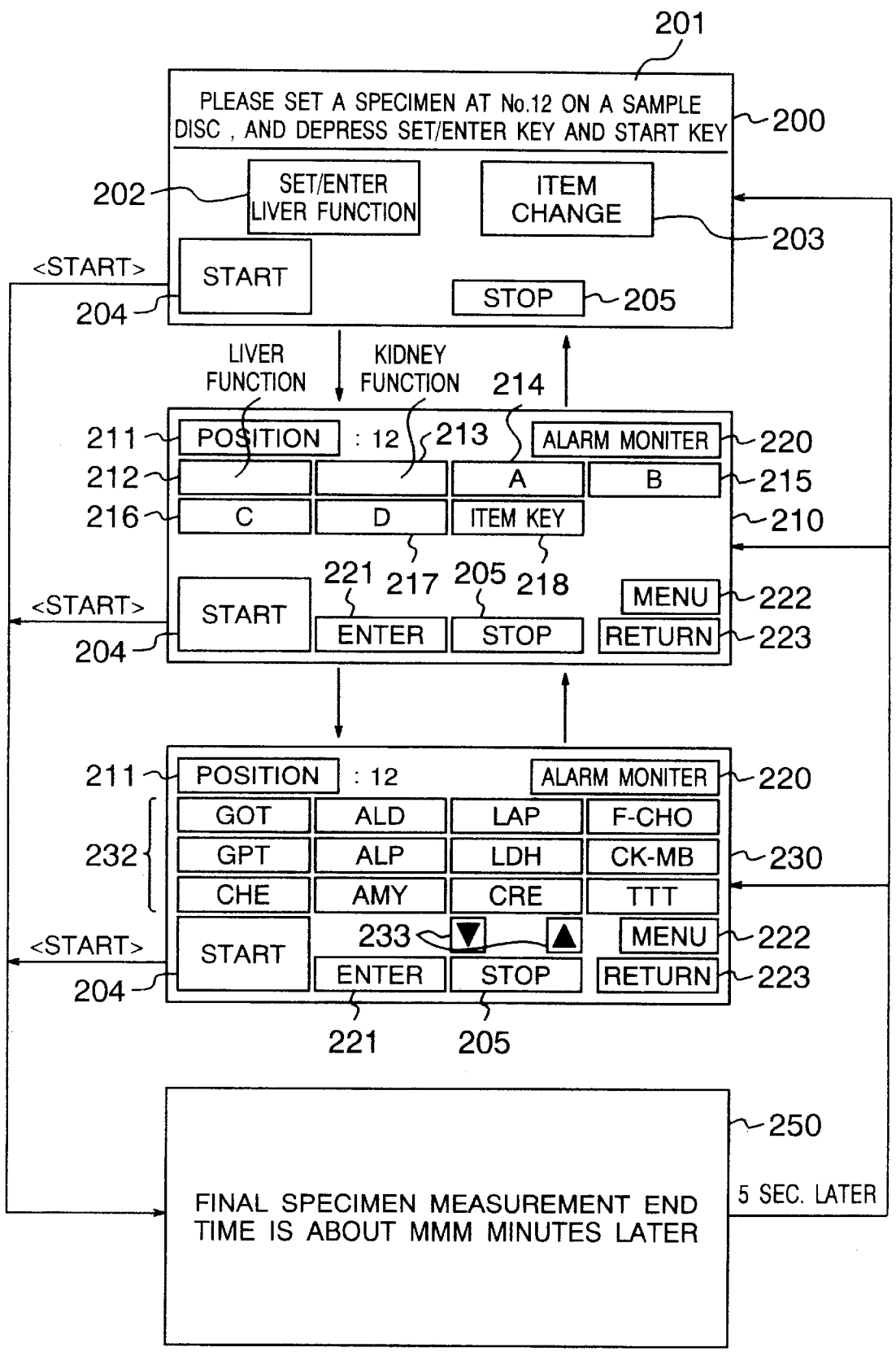
FIG. 12 illustrates the states of a display screen at respective steps of the flow chart.
Figure 13A:
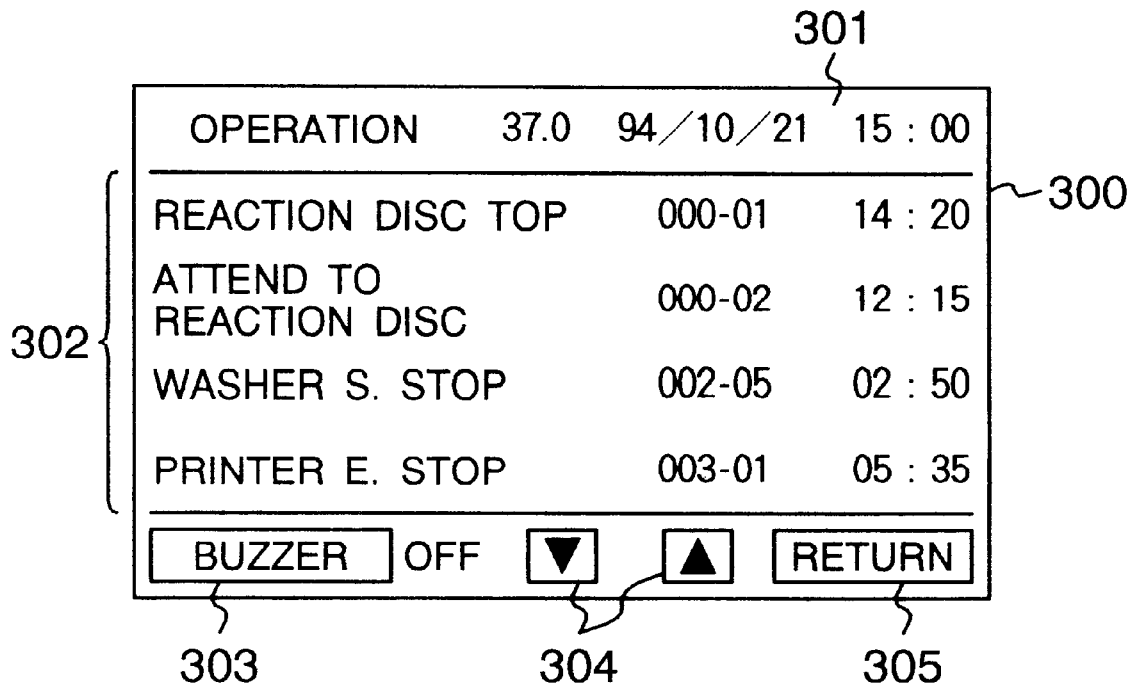
FIGS. 13A and 13B each show a display screen at an emergent stop.

FIG. 11 is a flow chart of an analyzing process and operation performed by the analyzer. FIG. 12 illustrates the states of the display screen at respective steps of the flow chart. FIGS. 13A and B each show a display screen at an emergent stop. Referring to those Figures, the analyzing process and operation performed by the analyzer will be described next. FIG. 12 shows that a specimen to be analyzed is set in a twelfth specimen container 11 and that what is set and entered is a liver faculty as an analysis item executed usually frequently.

(1) When the primary power supply switch of the analyzer is turned on (step 101) and the secondary power supply switch 43 is then turned on (step 102), a floppy disk mechanism 53 operates to thereby operate a heater 72 and maintain the reaction tank 7 and the electrolytic analyzer 70 at a constant temperature. Until this operation is completed, an indication "Please wait for 00 minutes" (not shown) is displayed on the input/output and display touch-paneled LCD 52. When those preparations are completed, a basic 1 display screen 200 is displayed automatically on the LCD 52 (step 103).

(2) At this time, as shown in FIG. 12, the LCD 52 displays the basic 1 display screen 200 which includes the address of the specimen container 11 in which a specimen is set, a character information display 201 which displays information reporting an analyzing process, a set/enter button 202 which selects item select information beforehand and specifies entered analysis, an item changing button 203 which changes the item select information, a start button 204 which starts the analysis, and a stop button 205 which stops the analysis during the analyzing operation. As described above, since the character information display 201 which reports the analyzing process and the button for operation are together provided, the operator is not required to turn his or her eyes this way and that, and is only required to operate the analyzer on the basis of the character information. Thus, the operation is simplified, and the operator is not required to worry about the operation, so that he or she can concentrate on handling the specimen container to thereby prevent a wrong specimen from being handled.

(3) Next, all reagents necessary for the analysis are set in the reagent disc 22 (step 104). Thereafter, a specimen is set at a position specified by the character information display unit 201 of the specimen table 12. Item select information is inputted for each specimen liquid. If beforehand entered item select information can be used as it is, item select information is specified with a set/enter button 202 (step 105). If the beforehand entered item select information is arranged to include item select information usually used frequently, such information is not required to be entered each time a specimen is analyzed, a wrong input operation is hence avoided and the operation time is reduced.

Item select information especially used frequently in a usual analysis is set in the set/enter button 202 of the basic 1 display screen 200 in the present invention. Item select information other than that set in the set/enter button 202 is set in a basic 2 display screen 210 to be described later, too. In addition, any detailed analysis item such as blood or urine can be selected in a basic 3 display screen 230 which will be described later, too.

Analysis conditions for each item select information are fed by a floppy disk. The analysis conditions are conditions of calculation of a light absorption degree of a specimen reaction liquid, an extracted quantity of a specimen, the conditions of extraction and injection of a first, a second and a third reagent, an analysis wavelength, a standard liquid concentration, a K factor, etc.

(4) The analysis of a specimen in accordance with item select information other than that in the set/enter button 202 of the basic 1 display screen 200 will be described next.

Although not shown in the flow chart of FIG. 11, in the analysis of a specimen in accordance with item select information other than that in the set/enter button 202, a change of item select information is specified by an item change button 203 on the basic 1 display screen 200. In response to this operation, a basic 2 display screen 210 appears which displays an indicator 211 indicating the address of a specimen container 11 in which the specimen is set. The address of the specimen container is also indicated on the basic 1 display screen 200.

First, a menu button 222 is depressed to display a menu display screen to confirm respective quantities of a reagent and a wash liquid as preparations for the analysis. The menu display screen is closed by a return button 223. After the preparations are completed, desired item select information is selected from among item select information buttons 211–217 in which corresponding item select information are beforehand set, and fixed by an enter button 221, and the analysis is started by a start button 204. A stop button 205 is depressed when the analysis is to be stopped.

Figure 13B:
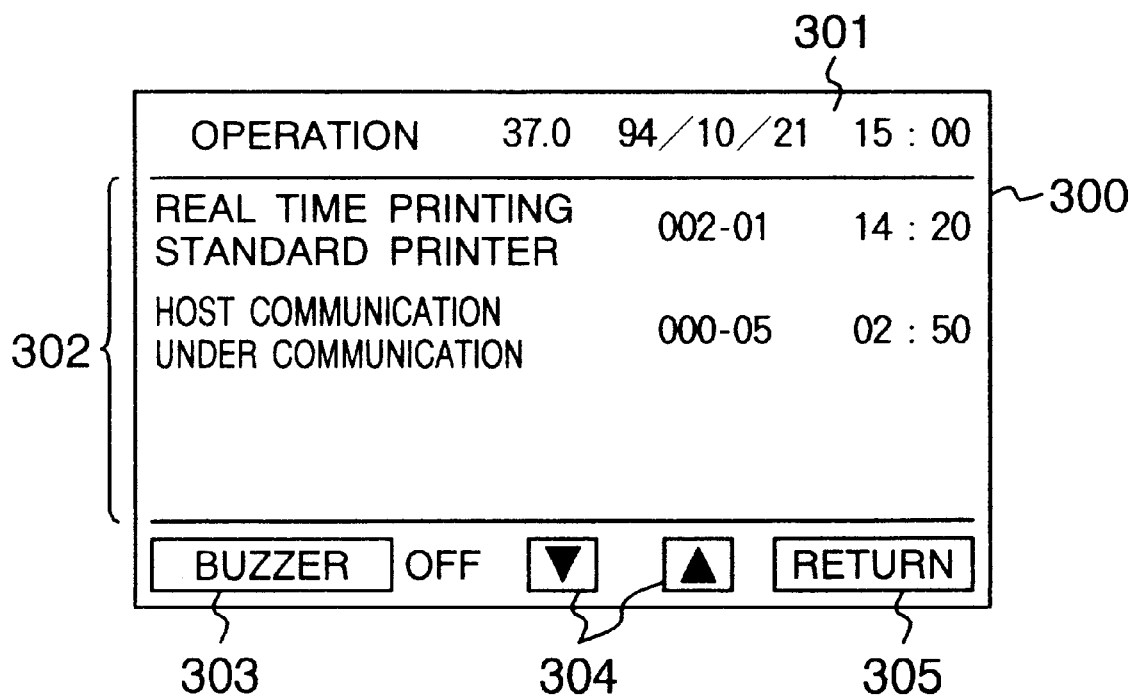

When the analyzer malfunctions, for example, the reaction disc 3 stops, or when handling is abnormal, for example, the specimen is not correctly set, an alarm monitor button 220 is lighted up and a buzzer is sounded to thereby inform the user of the occurrence of abnormality. If the basic 1 display screen 200 is displayed when the abnormality has occurred, the LCD 52 automatically displays the basic 2 display screen 210 and lights up an alarm monitor 220 to thereby sound the buzzer. When the operator or a responsible manager of the analyzer recognizes the occurrence of the abnormality with sounding of the buzzer and/or lighting up of the alarm monitor button 220 and presses the alarm monitor button 220, a display screen 300 which indicates the position of the abnormality of FIG. 13 appears which displays a title display screen 301 indicating the current date, time and temperature, an abnormal information list display screen 302 indicating the contents of the abnormality, an off button 303 which is used to stop the buzzer, a scroll button 304 which is used to scroll the abnormal information list display screen and a return button 305 which returns the abnormality display screen 300 to the basic display screen when the abnormality is confirmed.

As described above, since the abnormality display screen 300 displays a request number (corresponding to a specimen ID number), the current time, and the place and time of abnormality occurrence simultaneously, a lapsed time after the analyzer stopped can be known, the analyzer itself, specimen, and reagent can be treated appropriately. In whichever state the display screen of the LCD 52 may be, the basic 2 display screen is always displayed automatically, so that the abnormality can rapidly be coped with.

(5) The analysis of a specimen, using item select information other than the item select information set beforehand on the basic 2 display screen 210, will be described next. When an item key 218 on the basic 2 display screen 210 is specified, a basic 3 display screen 230 appears, which includes a display 211 which displays the address of a specimen container 11 in which a specimen is set. The basic 3 display screen 230 also has the menu button 222, return button 223, stop button 205, and alarm monitor button 220 of the basic 2 display screen 210, and the functions and operations of those elements are the same as those described about the basic 2 display screen.

Desired item select information is selected from among 40 analysis item buttons 232 such as, for example, for urine or blood, and fixed by the enter button 221, and its analysis is started by the start button 204. In the analyzer, only 12 analysis item buttons are displayed on a single display screen and as requested, the next analysis item buttons are called up with scroll buttons 233.

(6) When the above preparations are completed, the operator depresses the start button 204 to start the analyzer (step 106). In response to this operation, an analysis end time is displayed for five seconds on the LCD 52 and the first basic picture 200 is then displayed (step 107). As just described above, five seconds after setting one specimen is completed, the first basic picture 200 for setting the next specimen automatically is displayed. Therefore, the operator can rapidly set many specimens and also when another operator analyzes a specimen, he or she can set same rapidly.

(7) When the analysis ends (step 108), the operator is informed of the end of the analysis via a telephone line (step 110). Then, the result of the analysis is outputted by the output printer 51 (step 111). At the occurrence of abnormality, the second basic image 210 is displayed automatically, an alarm monitor 220 is lighted up, and the manager of the analyzer is informed of the presence of an alarm display (step 109). Even when the operator is remote from the analyzer or has forgotten the end time of the analysis, the operator can know the end of the analysis or the occurrence of the abnormality. Thus, the operator can concentrate on a thing other than the analysis and reduce his or her mental load.

Since the address of the specimen disc 12 on which a specimen is set is displayed on all basic first, second and third pictures 200, 210, and 230 of the LCD 52, the operator can easily recognize a place where the specimen is to be set and prevent the specimen from being wrongly set.

Figure 14:
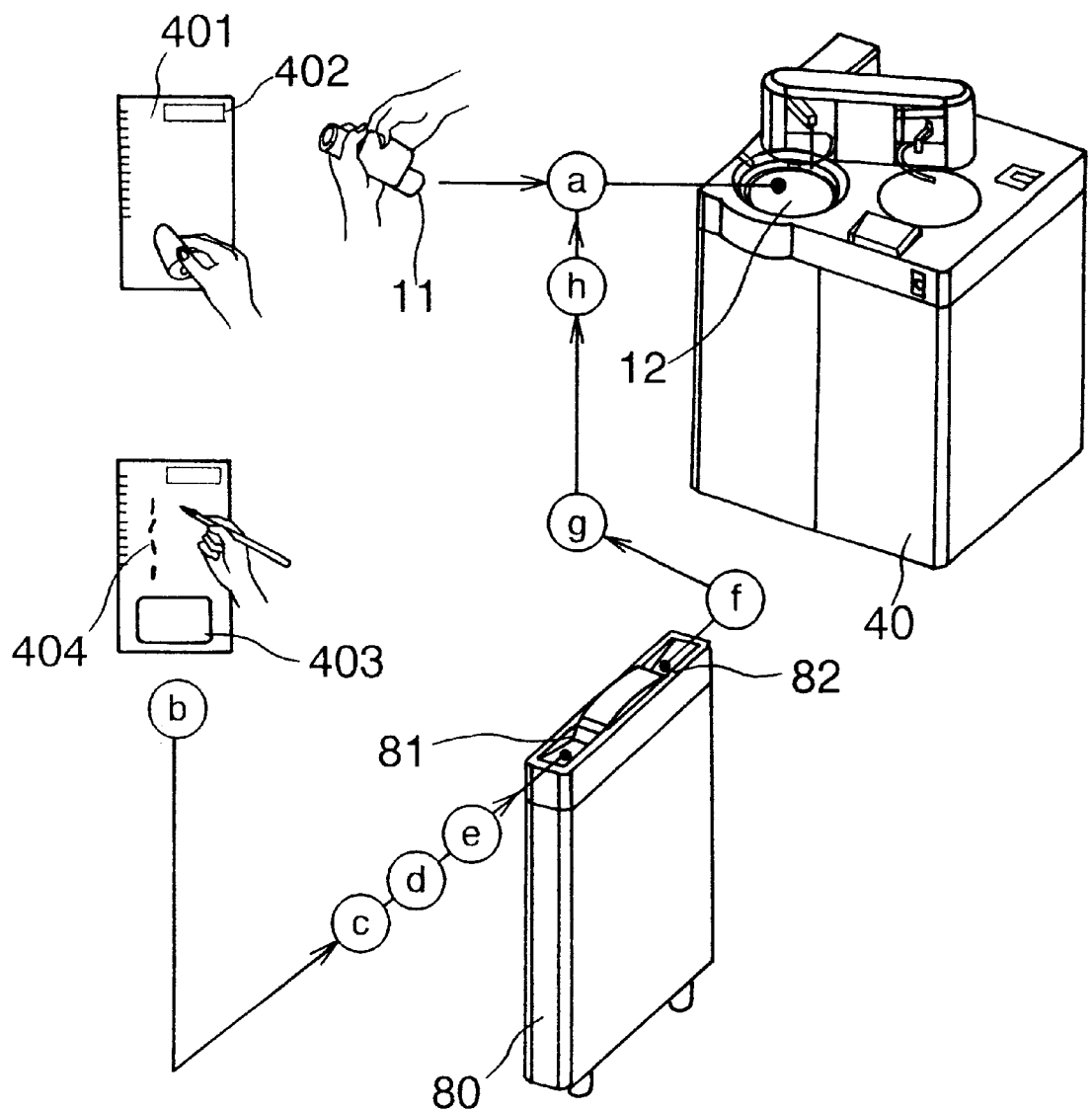
FIG. 14 illustrates an operating process in an emergent examination.
Figure 15:
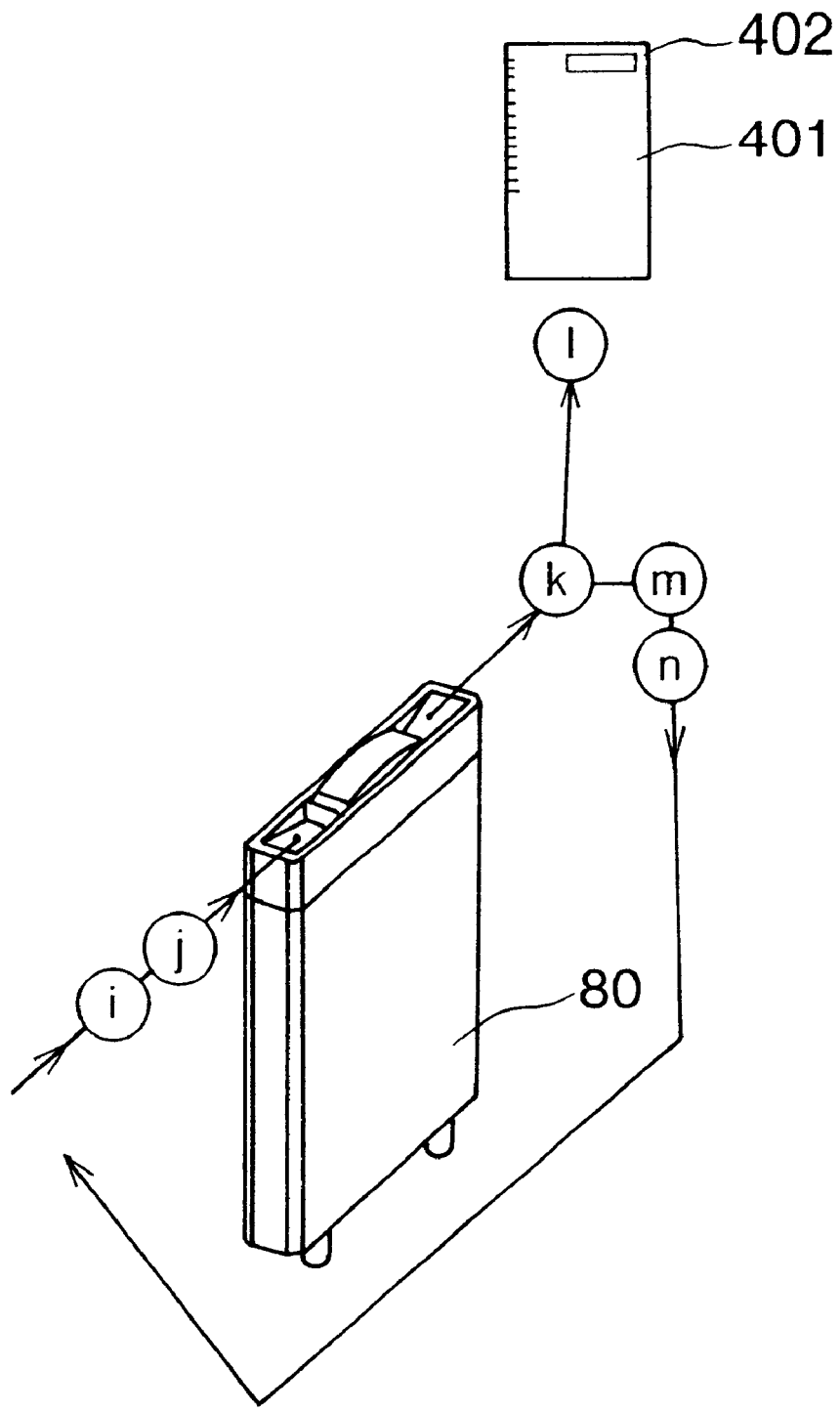
FIG. 15 illustrates a process for outputting the result of the analysis of FIG. 14.

Emergent analysis of a specimen will be described next. FIG. 14 shows a process for an emergent analysis of the specimen. FIG. 15 shows a process for outputting the result of the analysis of FIG. 14, in which the emergent analysis causes the analyzer to analyze the specimen and to output the result of the analysis on an examination card 401, which includes an examination request and a report, in accordance with an instruction of item select information. The examination card 401 has a request number 402 (corresponding to a specimen ID number) and a bar code label 403 indicative of the request number. The process for the emergent analysis will be described next with respect to FIGS. 14 and 15.

(a) The bar code label 403 pasted on the examination card 401 is torn off from same, and then pasted on a specimen container 11, which is then set on the specimen disc 12.

(b) Analysis items described on a mark sheet 404 of the examination card 401 are marked and desired item select information is specified.

(c) The examination card is then inserted into a card entrance 81 on the upper surface of the emergent examination device 80.

(d) The emergent examination device 80 reads a request number 402 on the examination card 401 and identifies its specimen ID information.

(e) The emergent examination device 80 reads and identifies item select information marked on the mark sheet 404 of the card 401.

(f) The emergent examination device 80 sends the item ID information and select information to the inventive analyzer.

(g) The examination card 401 is discharged from a card exit 82 provided on the upper surface of the emergent examination device 80.

(h) The above steps (a)–(g) are repeated on a second examination card 401 for the next specimen.

(i) The second examination card 401 read at step (c) is inserted into the card entrance 81.

(j) The emergent examination device 80 again reads a request number 402 on the second examination card 401 and identifies its specimen ID information.

(k) When all the results of the analyses requested by the examination card 401 read at step (i) are already collected, they are sent from the inventive analyzer to the emergent examination device 80.

(l) The emergent examination device 80 prints the result of the analysis on an analysis result output column 405 of the examination card 401.

(m) When all the results of the analyses are not yet collected, the examination card 401 is discharged from the emergent examination device 80.

(n) The above steps (i)–(m) are repeated for an examination card 401 for the further next specimen.

All the specimen ID information, item select information and the result of the analysis are printed as the result of the emergent examination on the examination card 401. Thus, even an unskilled operator can prevent misoperations and mistaking the result of the examination because the inventive analyzer checks the request number 402 pasted on the specimen container 11 with the request number 402 on the examination card 401 and then analyzes the specimen.

According to the invention, the analyzer is made compact, the cost is thus reduced, the operability of the analyzer and the environment of a clinical examination room are improved, and the operator's mental load in the operation of the analyzer is reduced. The present analyzer can easily be carried, for example, into the clinic examination room, only by opening one of a pair of doors of the room.

What is claimed is:

1. An automatic analyzer comprising a specimen container, a reagent container, a reactor container, a specimen extracting and injecting unit for extracting a part of a specimen from the specimen container and for injecting the extracted part of a specimen into the reaction container, and a reagent extracting and injecting unit for extracting a part of a reagent from the reagent container and for injecting the extracted part of a reagent into the reaction container to thereby cause the specimen to react with the reagent to analyze components of the specimen, the specimen container being disposed in an area proximate to a front edge of the analyzer, the reagent container being disposed at a position rearwardly and in an oblique direction with respect to a front portion of the specimen container, the reaction container being disposed at a position which is rearwardly with respect to the front portion of the specimen container and rearwardly with respect to a front portion the reagent container, said specimen extracting and injecting unit being disposed between the specimen container and the reaction container so that a first member supporting said specimen extracting and injecting unit is disposed at a position rearwardly of the specimen container, and said reagent extracting and injecting unit being disposed between the reagent container and the reaction container so that a second member supporting said reagent extracting and injecting unit is disposed at a position rearwardly of the reagent container, a cover member which is removable for covering said specimen extracting and injecting unit and said reagent extracting and injecting unit, wherein said cover member includes at least one opening through which an arm and a nozzle of said specimen extracting and injecting unit and an arm and a nozzle of said reagent extracting and injecting unit go in and out so as to be completely covered by said cover member in one position thereof and to extend outwardly from said cover member without being completely covered by said cover member in another position thereof, a specimen container cover for covering the specimen container and having a nozzle guard groove extending along an orbit of said specimen extracting and injecting unit, and a reagent container cover for covering the reagent container and having a nozzle guard groove extending along an orbit of said reagent extracting and injecting unit.

2. An automatic analyzer according to claim 1, wherein said cover member is made of a transparent material so that said cover member has transparency.

3. An automatic analyzer according to claim 1, wherein said cover member only covers said specimen extracting and injecting unit and said reagent extracting and injecting unit.

4. An automatic analyzer according to claim 1, wherein said cover member is configured so as to cover said specimen extracting and injecting unit and said reagent extracting and injecting unit and is removable from said automatic analyzer independent of positions of said specimen extracting and injecting unit and said reagent extracting and injecting unit.

5. An automatic analyzer according to claim 1, wherein said cover member is configured so as to have an inverted U-shape, said cover member having a first opening through which said arm and said nozzle of said specimen extracting and injecting unit goes in and out and a second opening through which said arm and said nozzle of said reagent extracting and injecting unit goes in and out.

6. An automatic analyzer according to claim 1, wherein each of said cover member, said specimen container cover and said reagent container cover is independently removable from said automatic analyzer.

* * * * *